United States Patent
Park et al.

(10) Patent No.: US 8,308,657 B2
(45) Date of Patent: Nov. 13, 2012

(54) APPARATUS FOR COLLECTING THE AMNIOTIC FLUID FROM THE UTERUS

(75) Inventors: Joong Shin Park, Seoul (KR); Bo Hyun Yoon, Seoul (KR); Jong Kwan Jun, Seoul (KR)

(73) Assignee: SNU R&DB Foundation, Seoul (KR)

( * ) Notice: Subject to any disclaimer, the term of this patent is extended or adjusted under 35 U.S.C. 154(b) by 859 days.

(21) Appl. No.: 12/306,472

(22) PCT Filed: Jan. 3, 2008

(86) PCT No.: PCT/KR2008/000031
§ 371 (c)(1),
(2), (4) Date: Dec. 23, 2008

(87) PCT Pub. No.: WO2008/082255
PCT Pub. Date: Jul. 10, 2008

(65) Prior Publication Data
US 2009/0281456 A1 Nov. 12, 2009

(30) Foreign Application Priority Data
Jan. 5, 2007 (KR) .................. 10-2007-0001364

(51) Int. Cl.
*A61B 5/00* (2006.01)
*A61F 2/02* (2006.01)
*B65D 81/00* (2006.01)

(52) U.S. Cl. ....................................... 600/582

(58) Field of Classification Search ............... 600/573, 600/581, 582; 128/837, 841
See application file for complete search history.

(56) References Cited

U.S. PATENT DOCUMENTS

| | | | |
|---|---|---|---|
| 3,952,737 A * | 4/1976 | Lipfert et al. ............... | 128/837 |
| 4,662,376 A | 5/1987 | Belanger | |
| 6,206,840 B1 | 3/2001 | Abraham-Fuchs et al. | |

FOREIGN PATENT DOCUMENTS

| | | |
|---|---|---|
| KR | 1020010110556 A | 12/2001 |
| WO | WO 85/04325 A1 * | 10/1985 |
| WO | WO 95/32672 | 12/1995 |
| WO | WO 2005/099599 | 10/2005 |

OTHER PUBLICATIONS

International Search report for PCT Application No. PCT/KR2008/000031; 2 pp., (Apr. 14, 2008).

* cited by examiner

*Primary Examiner* — Brian Szmal
(74) *Attorney, Agent, or Firm* — Klarquist Sparkman, LLP

(57) ABSTRACT

An apparatus is provided for collecting amniotic fluid from the uterus. In order to collect the amniotic fluid from the uterus through the external orifice of the cervix of a pregnant woman, an amniotic fluid collecting unit is adapted to bring a mouth, which is foldably formed at the upper end of an amniotic fluid collecting bag, into close contact with an end of the external orifice of the cervix. Thereby, the apparatus not only significantly decreases the risk occurring when a needle is directly inserted into the uterus in order to carry out the amniocentesis (amniotic fluid testing), but also eliminates pain and anxiety caused by the direct insertion of the needle.

7 Claims, 6 Drawing Sheets

APPARATUS FOR COLLECTING THE AMNIOTIC FLUID FROM THE UTERUS

CROSS REFERENCE TO RELATED APPLICATIONS

This is the U.S. National Stage of PCT Application No. PCT/KR2008/000031, filed Jan. 3, 2008, which was published in English under PCT Article 21(2), which in turn claims the benefit of Korean Application No. 10-2007-0001364, filed Jan. 5, 2007, which is incorporated herein by reference in its entirety.

TECHNICAL FIELD

The present invention relates, in general, to an apparatus for collecting amniotic fluid from the uterus through the cervix of a pregnant woman and, more particularly, to an apparatus for collecting amniotic fluid from the uterus through the external orifice of the cervix of a pregnant woman, in which the mouth of an amniotic fluid collecting bag is brought into close contact with the end of the external orifice of the cervix.

BACKGROUND ART

Within the uterus of a pregnant woman, a growing fetus is surrounded and cushioned by amniotic fluid, which is watery liquid within the amnion. Also, amniotic fluid is one of the main samples used for the medical examination of the pregnant woman and her fetus.

For gathering information about the fetus's health and development, particularly about the possibility of premature birth, amniotic fluid infection, fetal inflammation and infection, fetal damage, fetal maturity, fetal diseases and chromosomal abnormalities, and component analysis of amniotic fluid, amniocentesis (Transabdominal amniotic fluid collection) is carried out by inserting a thin, hollow needle through the abdomen into the uterus and taking a small sample of amniotic fluid. Currently, abdominal puncture with a needle for collecting amniotic fluid from the uterus is used for various amniotic fluid tests including the identification of fetal abnormality and amniotic fluid infection.

However, the insertion of the needle entails the risk of complications and medical accidents, causing anxiety and pain to the pregnant woman.

DISCLOSURE

Technical Problem

Accordingly, the present invention has been made keeping in mind the above problems occurring in the prior art, and an object of the present invention is to provide an apparatus for collecting amniotic fluid from the uterus, which can not only significantly decrease the risk occurring when a needle is directly inserted into the uterus in order to diagnose the possibility of premature birth, amniotic fluid infection, fetal inflammation and infection, fetal damage, fetal maturity, and fetus diseases and chromosomal abnormalities, and conduct component analysis on amniotic fluid, but also eliminate pain and anxiety caused by the direct insertion of the needle.

Technical Solution

In order to accomplish the above object, according to a first embodiment of the present invention, there is provided an apparatus for collecting amniotic fluid from the uterus, which comprises: an amniotic fluid collecting bag, which is provided at a lower end of the external orifice of the cervix so as to collect the amniotic fluid from the uterus through the external orifice of the cervix; and an amniotic fluid collecting unit, which brings the amniotic fluid collecting bag into close contact with the lower end of the external orifice of the cervix.

Here, the amniotic fluid collecting bag includes a mouth, which is folded to a predetermined length at an upper end thereof so as to be in close contact with the lower end of the external orifice of the cervix.

Further, the mouth of the amniotic fluid collecting bag can be expanded by the amniotic fluid collecting unit so that the amniotic fluid collecting bag can be brought into close contact with the lower end of the external orifice of the cervix.

Also, the amniotic fluid collecting bag is made of a material harmless to the human body, which is selected from natural rubber and urethane.

Further, the mouth of the amniotic fluid collecting bag is made of a hydrophilic material.

Meanwhile, the amniotic fluid collecting unit includes a cylindrical contact guide, which extends from a handle having an O-ring shape in one direction.

In addition, the number of contact guides is at least two.

According to a second embodiment of the present invention, there is provided an apparatus for collecting amniotic fluid from the uterus, which comprises: an amniotic fluid collecting bag, which includes a mouth, which is folded at a predetermined length at an upper end thereof so as to be in close contact with a lower end of the external orifice of the cervix in order to collect the amniotic fluid from the uterus through the external orifice of the cervix; and an amniotic fluid collecting unit, which expands the mouth so as to bring the amniotic fluid collecting bag into close contact with the lower end of the external orifice of the cervix.

Here, the amniotic fluid collecting bag is made of a material harmless to the human body, which is selected from natural rubber and urethane.

Further, the mouth of the amniotic fluid collecting bag is made of a hydrophilic material.

In addition, the amniotic fluid collecting unit has a hollow cylindrical shape.

Advantageous Effects

With the apparatus for collecting amniotic fluid from the uterus according to the present invention, in order to collect the amniotic fluid from the uterus through the external orifice of the cervix of a pregnant woman, an amniotic fluid collecting unit is adapted to bring a mouth, which is foldably formed at the upper end of an amniotic fluid collecting bag, into close contact with an end of the external orifice of the cervix. Thereby, the apparatus can not only significantly decrease the risk occurring when a needle is directly inserted into the uterus for the acquisition of amniotic fluid in order to diagnose the possibility of premature birth, amniotic fluid infection, fetal inflammation and infection, fetal damage, fetal maturity, and fetal diseases and chromosomal abnormalities, and perform component analysis on amniotic fluid, but also eliminate pain and anxiety caused by the direct insertion of the needle.

DESCRIPTION OF SYMBOLS OF THE MAIN PARTS IN THE DRAWINGS

1: reproductive organ
10: uterus
20: oviduct
30: ovary
40: cervix
43: internal orifice of cervix
45: external orifice of cervix
47: vagina
49: orifice of vagina
50: amniotic fluid collecting bag
53: mouth of amniotic fluid collecting bag
60, 70: amniotic fluid collecting unit
63, 73: contact guide
65: handle

BEST MODE

Hereinbelow, the embodiments of the present invention will be described in detail with reference to the accompanying drawings.

Figure 1:
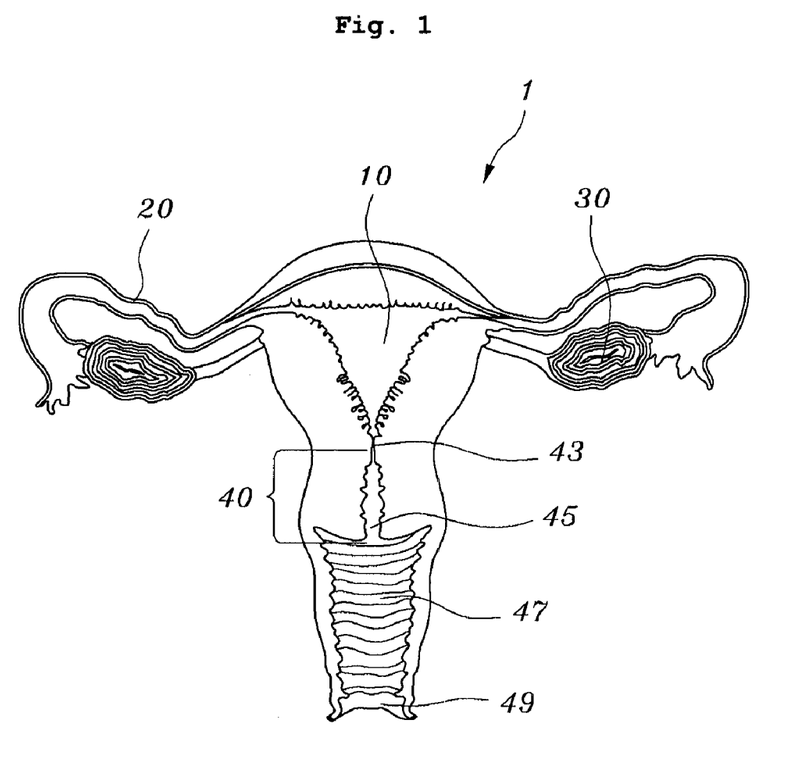
FIG. 1 is a sectional view illustrating a female reproductive organ.
Figure 2:
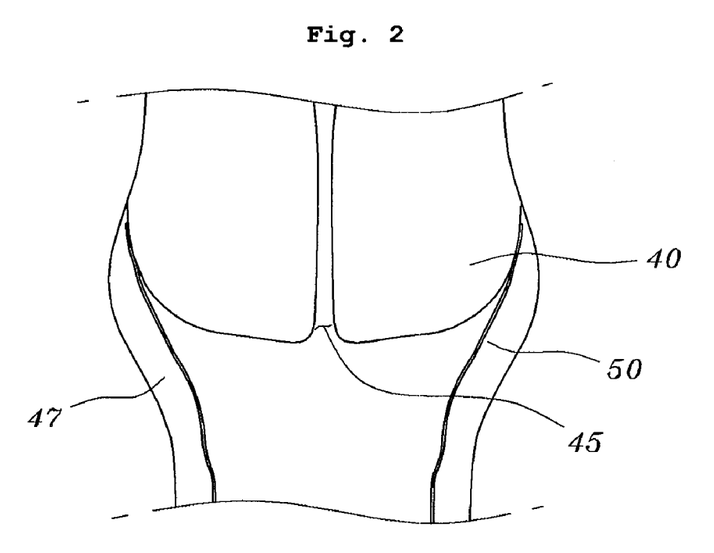
FIG. 2 is an enlarged sectional view illustrating the state in which an amniotic fluid collecting bag is in close contact with the cervix in accordance with a first embodiment of the present invention.
Figure 3:
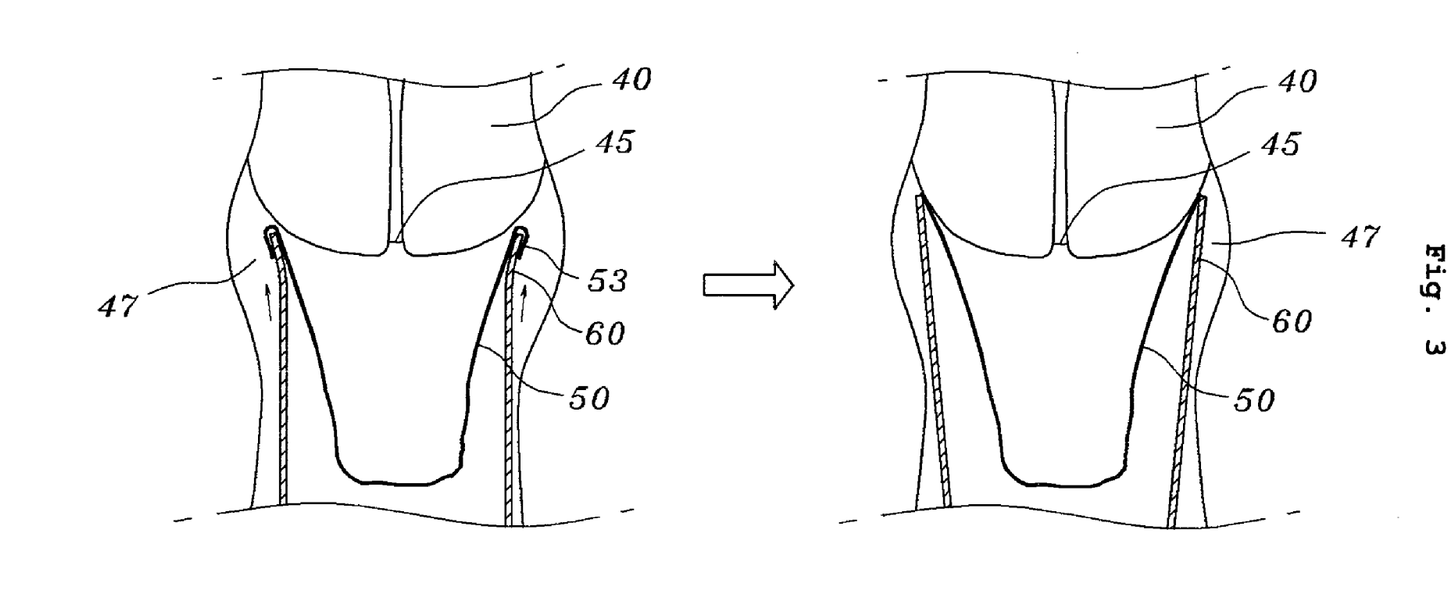
FIG. 3 is an enlarged sectional view illustrating the process of bringing an amniotic fluid collecting bag into close contact with the cervix in accordance with a first embodiment of the present invention.
Figure 4:
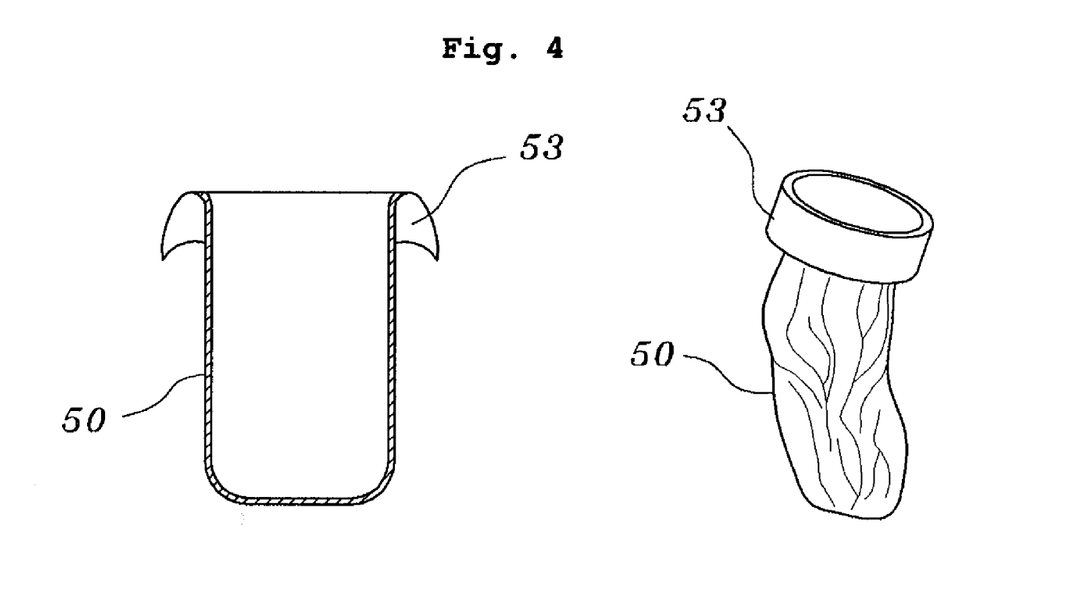
FIG. 4 is a sectional view and a perspective view of an amniotic fluid collecting bag in accordance with a first embodiment of the present invention.
Figure 5:
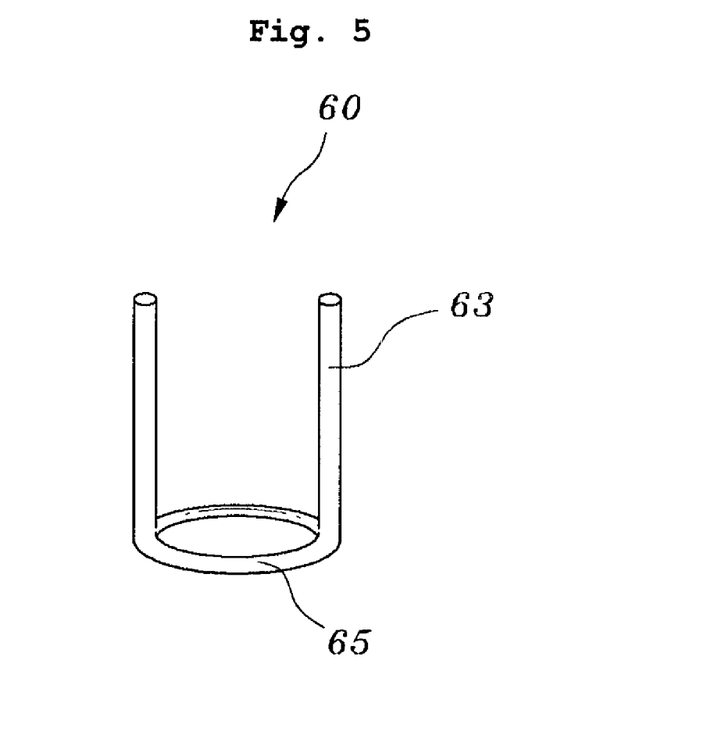
FIGS. 5, 6 and 7 are schematic perspective views illustrating an amniotic fluid collecting unit in accordance with a first embodiment of the present invention and its variations.
Figure 6:
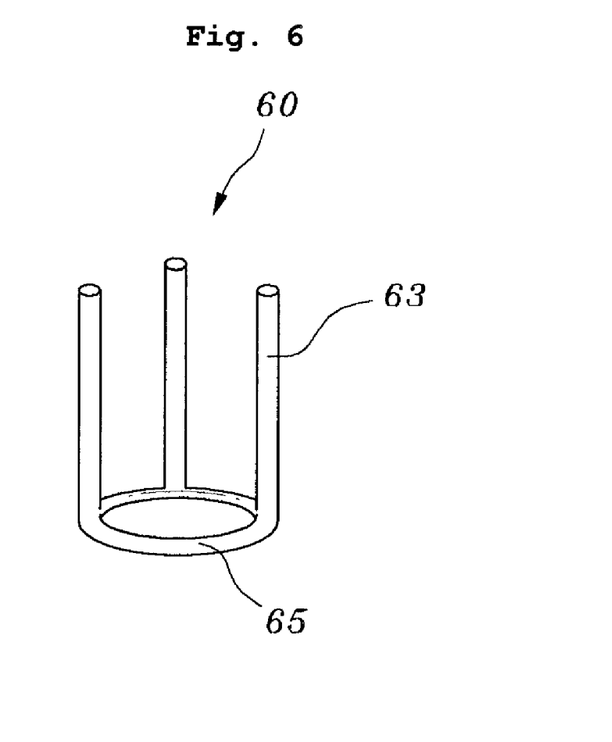
Figure 7:
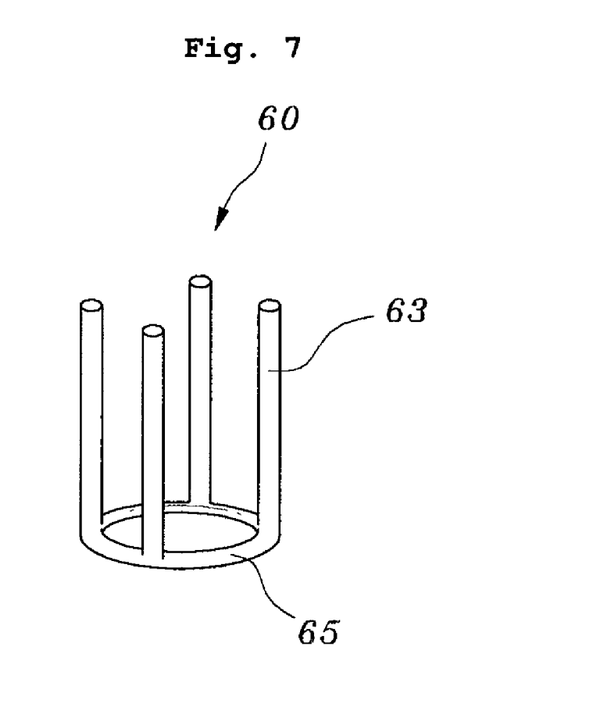
Figure 8:
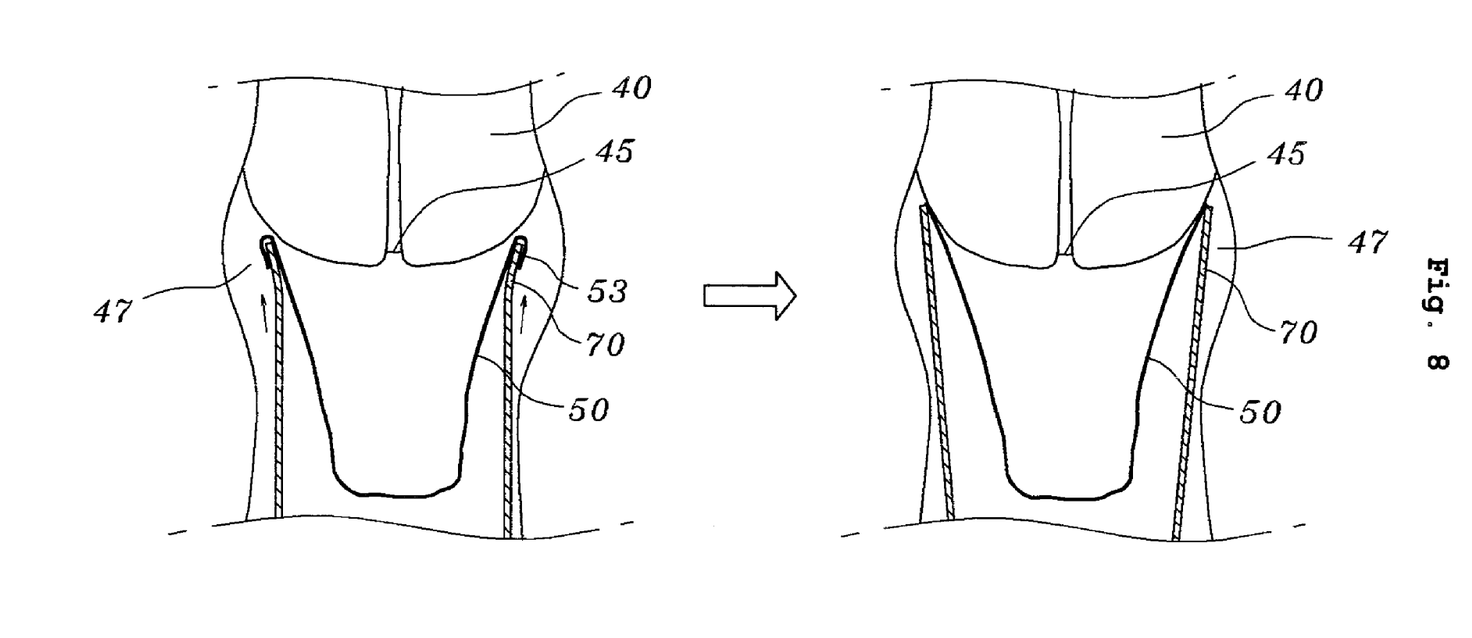
FIG. 8 is an enlarged sectional view illustrating the process of bringing an amniotic fluid collecting bag into close contact with the cervix in accordance with a second embodiment of the present invention.
Figure 9:
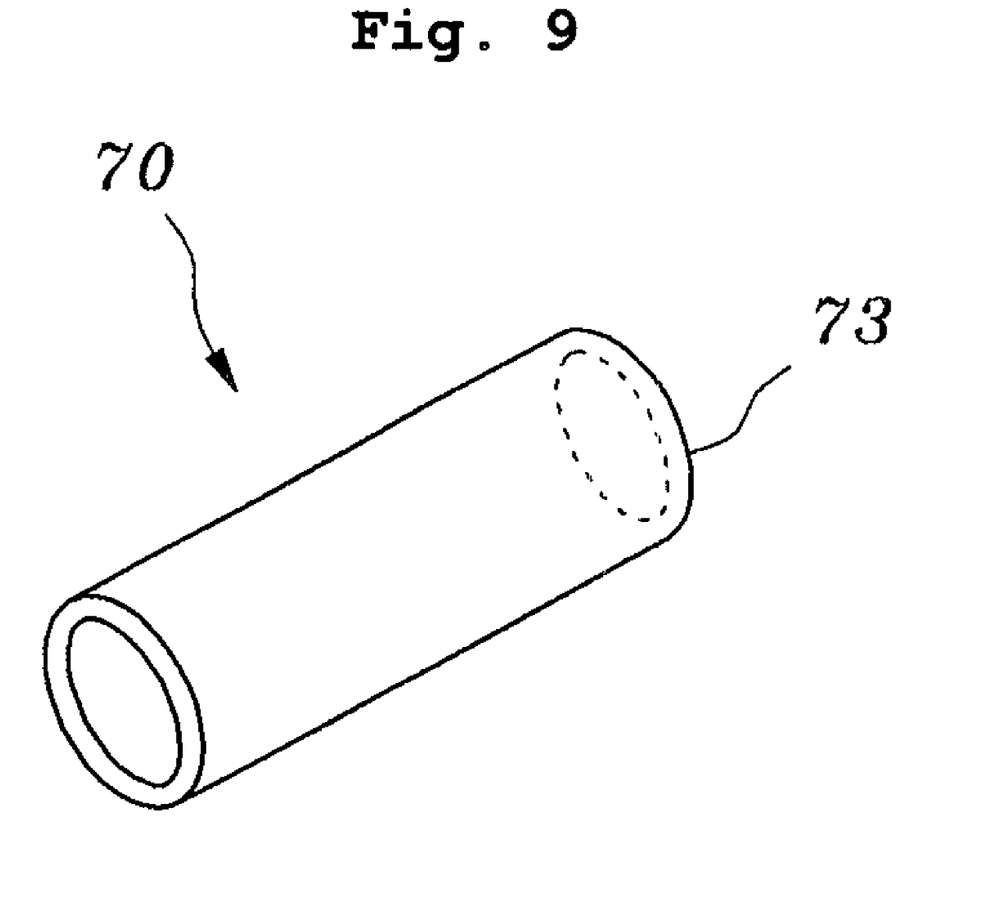
FIG. 9 is a schematic perspective view illustrating an amniotic fluid collecting unit in accordance with a second embodiment of the present invention.

FIG. 1 is a sectional view illustrating a female reproductive organ. FIG. 2 is an enlarged sectional view illustrating the state in which an amniotic fluid collecting bag is in close contact with the cervix in accordance with a first embodiment of the present invention. FIG. 3 is an enlarged sectional view illustrating the process of bringing an amniotic fluid collecting bag into close contact with the cervix in accordance with a first embodiment of the present invention. FIG. 4 is a sectional view and a perspective view illustrating an amniotic fluid collecting bag in accordance with a first embodiment of the present invention. FIGS. 5, 6 and 7 are schematic perspective views illustrating an amniotic fluid collecting unit in accordance with a first embodiment of the present invention and its variations. FIG. 8 is an enlarged sectional view illustrating the process of bringing an amniotic fluid collecting bag into close contact with the cervix in accordance with a second embodiment of the present invention. FIG. 9 is a schematic perspective view illustrating an amniotic fluid collecting unit in accordance with a second embodiment of the present invention.

As illustrated in FIG. 1, a female reproductive organ 1 comprises an orifice of a vagina 49 and a vagina 47 which are external reproductive organs, and a uterus 10, oviducts (Fallopian tubes) 20, and ovaries 30 which ate internal reproductive organs.

The ovaries 30 produce ova and secret female hormones.

When attaining the age of puberty, a woman starts to undergo ovulation, which is the process in the menstrual cycle by which a mature ovarian follicle ruptures and releases an ovum from one of the ovaries 30.

Normally, each of the ovaries 30 releases an ovum every other month, so that an ovum is released at every menstrual cycle.

With the onset of ovulation, the uterine lining (endometrium) is thickened. Unless a fertilized egg is implanted on the uterine wall, the thickened uterine lining is shed, resulting in menstrual bleeding.

Menstruation occurs roughly once per month, but many women suffer from irregular menstrual cycles, particularly for one or two years after their first menstruation, and even into marriage.

The ovaries 30 are located at bilateral rear upper sides of the uterus 10. The ovaries in females are homologous to the testes in males. That is, the ovaries produce, develop and release ova, and secrete female hormones.

In size, the ovary 30 varies depending on age. In the case of adults, before menopause, the ovary is as large as an apricot, while after menopause, the ovary significantly decreases in size, and is slightly larger than a small bean.

The uterus 10 mostly consists of thick, smooth muscle, which is expandable enough to accommodate a fetus just before childbirth.

The uterus 10 looks like a western pear, and varies in size. The main function of the uterus 10 is to accept a fertilized ovum which becomes implanted in the endometrium, and to develop an embryo and a fetus. Additionally, the uterus is responsible for menstruation.

The uterus 10 is vacant in non-pregnant women. It is located inside the pelvis immediately dorsal to the urinary bladder and ventral to the rectum.

The vagina 47 is a fibromuscular tubular tract leading from the uterus 10 to the exterior of the body in females.

Although there is wide anatomical variation, the length of the vagina of a virgin is approximately 7 to 10 cm. The vagina connects the superficial vulva to the cervix 40 of the uterus. The vagina has several biological functions: a passageway for menstrual blood and tissue to leave the body and a sexual organ.

During childbirth, the vagina provides the channel to deliver the baby from the uterus outside the body of the mother. Vaginal lubrication is provided by the glands near the internal orifice 43 and the external orifice 45 of the cervix. The membrane of the vaginal wall also produces moisture, although it does not contain any glands, because the cervical mucus glands secrete different kinds of mucus.

Keeping a low pH environment, the vaginal mucus prevents an infection and restrains bacterial flora from the vagina.

The labia minora (not shown) are situated between the labia majora (not shown), which are lip-like structures comprised mostly of skin and adipose tissue, with the clitoris prepuce surrounding the upper region thereof. There are no hair follicles in the labia minora. During sexual arousal, the labia become engorged with blood, typically swelling slightly and darkening or reddening in color.

Mode for Invention

In the first embodiment of the present invention, as illustrated in FIGS. 2 through 5, in order to collect the amniotic fluid passed through the external orifice 45 of the cervix 40 of the pregnant woman, an amniotic fluid collecting unit 60 (see FIG. 5) is adapted to bring a mouth 53, which is foldably formed at the upper end of an amniotic fluid collecting bag 50 (see FIG. 4), into close contact with an end of the external orifice of the cervix 40. Thereby, the amniotic fluid can be collected into the amniotic fluid collecting bag 50.

At this time, the amniotic fluid collecting unit 60 comprises a handle 65 having the shape of an O-ring, and a plurality of cylindrical contact guides 63 extending from the handle 65 in one direction.

Now, the process of collecting the amniotic fluid will be described in detail.

First, the contact guides 63 of the amniotic fluid collecting unit 60 are fixed to the folded mouth 53 of the amniotic fluid collecting bag 50.

The contact guides 63 are brought into contact with the end of the external orifice of the cervix 40 through the vagina 47.

The mouth 53 of the amniotic fluid collecting bag 50, which is in contact with the end of the external orifice of the cervix 40 in a circumferential direction, is further pushed in an upward direction using the handle 65 of the amniotic fluid collecting unit 60, so that the mouth 53 is uniformly expanded by the contact guide 63, and thus is brought into close contact with the end of the external orifice of the cervix 40 in a desired shape.

Thus, the amniotic fluid passed through the external orifice 45 of the cervix 40 is collected into the amniotic fluid collecting bag 50. Thereby, the amniotic fluid that obtained by this present invention can process the same characteristics as that taken using the needle, which is directly inserted into the uterus through the abdomen of the pregnant woman.

In the first embodiment of the present invention, the amniotic fluid collecting unit 60 shows that the number of cylindrical contact guides 63, which extend from the O-ring shaped handle 65 in one direction, is two. However, as illustrated in FIGS. 6 and 7, the number of cylindrical contact guides 63 can be changed to another number, for instance, three or four. In addition, the shape of the contact guide 63 can be changed to one of various other shapes.

Since a variety of tests can be performed on the pregnant woman and her fetus using the amniotic fluid obtained and collected in this way, the amniotic fluid collecting unit can not only significantly decrease the pain and anxiety in the pregnant woman, compared to the case where the amniotic fluid is taken using the needle that is directly inserted into the uterus through the abdomen of the pregnant woman, but also be free from the risk of the outbreak of complications and medical accidents, which may take place upon the direct insertion of the needle into the uterus.

At this time, the amniotic fluid collecting bag 50 is preferably formed of a material harmless to the body, such as natural rubber or urethane, because it is inevitably in contact with the linings of the cervix 40 and the vagina 47 of the pregnant woman.

Further, the amniotic fluid collecting bag 50 is preferably made of a hydrophilic material such that the mouth 53 thereof can be in close contact with the end of the external orifice of the cervix 40 in a desired shape.

Meanwhile, in the second embodiment of the present invention, as illustrated in FIGS. 8 and 9, in order to collect the amniotic fluid passed through the external orifice 45 of the cervix 40 of the pregnant woman, an amniotic fluid collecting unit 70 (see FIG. 9) is adapted to bring a mouth 53, which is foldably formed at the upper end of an amniotic fluid collecting bag 50, into close contact with an end of the external orifice of the cervix 40 using a contact guide 73. Thereby, the amniotic fluid can be collected into the amniotic fluid collecting bag 50.

At this time, the amniotic fluid collecting unit 70 preferably has a hollow cylindrical shape.

Now, the process of collecting the amniotic fluid will be described in detail.

First, the contact guide 73, which is located at an upper end of the amniotic fluid collecting unit 70, is contacted with and fixed to the folded mouth 53 of the amniotic fluid collecting bag 50 in an inner circumferential direction.

The amniotic fluid collecting unit 70 is inserted into the orifice 49 of the vagina, and thereby the contact guide 73 comes into contact with the end of the external orifice of the cervix 40 via the vagina 47.

The mouth 53 of the amniotic fluid collecting bag 50, which is in contact with the end of the external orifice of the cervix 40 in a circumferential direction, is further pushed in an upward direction using a lower end of the amniotic fluid collecting unit 70, so that the mouth 53 is uniformly expanded by the contact guide 73 of the amniotic fluid collecting unit 70, and thus is brought into close contact with the end of the external orifice of the cervix 40 in a desired shape.

Thus, the amniotic fluid passed through the external orifice 45 of the cervix 40 is collected into the amniotic fluid collecting bag 50. Thereby, amniotic fluid that obtained by this present invention can produce the same characteristics as that taken using the needle, which is directly inserted into the uterus through the abdomen of the pregnant woman.

Since a variety of tests can be performed on the pregnant woman and her fetus using the amniotic fluid obtained and collected in this way, the amniotic fluid collecting unit can not only significantly decrease the pain and anxiety in the pregnant woman, compared to the case where the amniotic fluid is taken using the needle that is directly inserted into the uterus through the abdomen of the pregnant woman, but also be very free from the risk of complications and medical accidents, which may take place upon the direct insertion of the needle into the uterus.

The amniotic fluid collecting bag 50 is preferably formed of a material harmless to the body, such as natural rubber or urethane, because it is inevitably in contact with the linings of the cervix 40 and the vagina 47 of the pregnant woman.

Further, the amniotic fluid collecting bag 50 is preferably made of a hydrophilic material such that the mouth 53 thereof can be in close contact with the end of the external orifice of the cervix 40 in a desired shape.

Although the exemplary embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An apparatus for collecting amniotic fluid from the uterus, comprising:
   an amniotic fluid collecting bag configured to be positioned at a lower end of the external orifice of the cervix so as to collect the amniotic fluid from the uterus through the external orifice of the cervix; and
   an amniotic fluid collecting unit configured to bring the amniotic fluid collecting bag into contact with the lower end of the external orifice of the cervix,
   wherein the amniotic fluid collecting bag includes a mouth, the mouth being folded at a predetermined length at an upper end thereof so as to be in contact with the lower end of the external orifice of the cervix, wherein the amniotic fluid collecting unit includes a cylindrical contact guide, which extends from a handle having an O-ring shape in one direction, and where the mouth is configured to be expanded by the contact guide so as to be in contact with the lower end of the external orifice of the cervix.

2. The apparatus according to claim 1, wherein the amniotic fluid collecting bag is made of a material selected from natural rubber and urethane.

3. The apparatus according to claim 1, wherein the mouth of the amniotic fluid collecting bag is made of a hydrophilic material.

4. The apparatus according to claim 1, wherein the apparatus comprises a plurality of contact guides.

5. An apparatus for collecting amniotic fluid from the uterus, comprising:

an amniotic fluid collecting bag, which includes a mouth configured to be folded at a predetermined length at an upper end thereof so as to be in contact with a lower end of the external orifice of the cervix in order to collect the amniotic fluid from the uterus through the external orifice of the cervix; and an amniotic fluid collecting unit configured to bring the amniotic fluid collecting bag into contact with the lower end of the external orifice of the cervix, wherein the amniotic fluid collecting unit has a hollow cylindrical shape, and wherein the mouth is configured to be expanded by a contact guide of the amniotic fluid collecting unit so as to be in contact with the lower end of the external orifice of the cervix.

6. The apparatus according to claim 5, wherein the amniotic fluid collecting bag is made of a material selected from natural rubber and urethane.

7. The apparatus according to claim 5, wherein the mouth of the amniotic fluid collecting bag is made of a hydrophilic material.

* * * * *